United States Patent [19]

Slettenmark

[11] Patent Number: 5,512,048
[45] Date of Patent: Apr. 30, 1996

[54] METHOD FOR CLEANING THE CATHETER OF AN IMPLANTED MEDICATION INFUSION SYSTEM

[75] Inventor: Bruno Slettenmark, Jaerfaella, Sweden

[73] Assignee: Siemens Elema AB, Solna, Sweden

[21] Appl. No.: 398,806

[22] Filed: Mar. 6, 1995

[30] Foreign Application Priority Data

Mar. 10, 1994 [SE] Sweden ................................. 9400823

[51] Int. Cl.⁶ ................................................. A61M 5/142
[52] U.S. Cl. ................................. 604/93; 604/49; 604/51; 604/131; 604/267
[58] Field of Search ............................ 604/280, 266, 604/267, 27, 28, 35, 48, 49, 51, 131, 93, 175

[56] References Cited

U.S. PATENT DOCUMENTS

| | | |
|---|---|---|
| 701,075 | 5/1902 | McCully . |
| 4,227,533 | 10/1980 | Godfrey . |
| 4,228,802 | 10/1980 | Trott .................................. 604/267 X |
| 4,854,325 | 8/1989 | Stevens . |
| 4,894,056 | 1/1990 | Bommarito ............................. 604/267 |
| 5,281,205 | 1/1994 | McPherson ............................ 604/267 |
| 5,397,340 | 3/1995 | Nyman . |

FOREIGN PATENT DOCUMENTS

| | | |
|---|---|---|
| WO89/07466 | 8/1989 | WIPO . |
| WO92/12756 | 8/1992 | WIPO . |

*Primary Examiner*—John D. Yasko
*Attorney, Agent, or Firm*—Hill, Steadman & Simpson

[57] ABSTRACT

Known implanted medication infusion systems have a medication container and a pump for pumping medication from the medication container into the patient via a catheter connected to the output of the pump. A flushing port is arranged downstream of the pump and upstream of the catheter. In a method for cleaning the catheter, a cleaning fluid is flushed through the flushing port and into the catheter. The orifice of the catheter is, during cleaning, placed in communication with the exterior of patient, and is isolated from the interior of the patient in order to convey the cleaning fluid out of the patient.

24 Claims, 3 Drawing Sheets

METHOD FOR CLEANING THE CATHETER OF AN IMPLANTED MEDICATION INFUSION SYSTEM

BACKGROUND OF THE INVENTION

1. Field of the Invention

The present invention relates to a method for cleaning the catheter of an implanted medication infusion system, the system being of the type having a medication container and a pump for pumping medication from the medication container into the patient via a catheter connected to the output of the pump, with a flushing port arranged downstream of the pump and upstream of the catheter for flushing a cleaning fluid through the flushing port and out into the catheter.

2. Description of the Prior Art

Current implantable medication infusion systems include a dosing unit; comprising a pump and a medication container, attendant electronics, a source of energy and a catheter which delivers medication to the intended site in the patient. The tip of the catheter can be located e.g., in a blood vessel, inside an organ, in body tissue or in the peritoneum. The internal diameter of the catheter is small, typically 0.3 mm, for a number of reasons, and occlusion of the catheter is the most common cause of faults in the system. Experience has shown that it takes about 12 months for occlusion or overgrowth of insulin catheters to develop in known systems. This time can vary widely from one person to another but is unacceptably brief in view of the approximate 5-year service life of the infusion system. Therefore either the catheter must be replaced a number of times during the system's service life, a measure requiring surgery, or attempts must be made to flush out the blockage with a neutral solution harmless to the patient.

Remedying catheter blockage by replacing the catheter requires surgery, as noted above, and is relatively expensive and infection in the implant pocket is also a risk, removal of the entire implant then often being necessary, causing the patient discomfort and inconvenience and requiring a special appointment to remove stitches.

Flushing away blockage in the catheter can sometimes be successful. The infusion system must then be equipped with a flushing port with a rubber septum through which a transcutaneous cannula is inserted, so a syringe can be used for flushing with a suitable solution, harmless to the patient, at a high pressure of about 10–20 bars. In this way the catheter occlusion can be forced out and possible overgrowth on the tip of the catheter can be pushed away. Although less invasive than surgery, this method still presents risks to the patient and to the implanted system.

This is in part because modified medication, such as modified insulin, crystallized insulin etc. which is often a major component in the occlusion, could be flushed into the patient's body with the risk that antibodies are formed in the patient against the medication as a negative consequence. There is also a considerable risk of damage to or destruction of the catheter, the catheter connection and the flushing port septum, or the catheter tip could be, in effect, "blown off" by the high pressure. Damage to parts on the output side of the pump by the high pressure is another risk. Aging of the polymer materials exposed to body fluids increases this risk with the age of the catheter.

Moreover, at every flushing occasion the patient receives a relatively high dose of medication, corresponding to the total volume of the flushing port and the catheter. This dose also depends on the concentration of the medication. In the case of insulin, it may be necessary to balance this dose with a concomitant glucose infusion. The aforementioned total volume can typically amount to 100 µl, the momentary dose then being 10 U of insulin when a solution of 100 U/ml of insulin is used, and 40 U of insulin when 400 U/ml insulin is used. Such doses could be directly fatal to many patients if the simultaneous glucose supply is insufficient.

Further, after the flushing event the flushing port and the catheter are filled with, typically, 100 µl of neutral liquid. When the pump is reactivated, the medication therefore mixes with this liquid in the flushing port, and the concentration of the pumped medication will rise only gradually to the correct value. This variation in the concentration is difficult to predict, since there is no active stirring, and the concentration of the pumped medication will fluctuate for a longer period of time with deviations in the prescribed insulin flow as a result.

Flushing with pressurized liquid at high pressure can at best remove a mechanical blockage in the catheter and restore the flow through the catheter. Nonetheless, deposits and residues of precipitated medication and adsorbed proteins will almost certainly remain on the interior surfaces of the catheter and these residues will then serve as "seeds" for new deposits of medication and will cause new catheter blockages in a relatively short time.

SUMMARY OF THE INVENTION

The above object is achieved in accordance with the principles of the present invention in a method for cleaning the catheter of a medication infusion system having a medication container, a pump for pumping medication from the medication container into the patient via a catheter connected to the output of the pump, and a flushing port disposed downstream of the pump and upstream of the catheter for flushing a cleaning fluid through the flushing port and out into the catheter, wherein the orifice of the catheter, during cleaning, is placed in communication with the exterior of the patient and is isolated from the interior of the patient, in order to convey cleaning fluid flushed through the flushing port out of the patient. The orifice of the catheter can be placed in communication with the exterior of the patient either by bringing the tip of the catheter out of the patient through a very small incision prior to flushing the catheter with cleaning fluid, or by introducing a small trocar through the abdominal wall of the patient which encloses and seals the catheter tip in situ, so that the cleaning fluid can be discharged to the exterior of the patient through the trocar in the abdominal wall.

With the method according to the invention, catheter lockages can thus be efficiently remedied without replacing the catheter and employing only minor surgery. The patient ill probably be able to leave the hospital immediately after the operation and will not need a new appointment for removal of stitches. In addition, the risk of infection, which is always present when the implant pocket is opened for catheter replacement, is avoided. Such an infection often makes necessary explantation of the entire infusion system and preparation of a new implant pocket at some other site or, alternatively, reimplantation at the same site after the infection has abated. With the method according to the invention, the pathway formed by the flushing port and the catheter is isolated from the patient, so no cleaning liquids, cleaning gases or material flushed from the catheter can enter the patient's body. As a result, any kind of cleaning liquid can be used, in principle, even aggressive fluids for chemical dissolution of the occlusion. Moreover, high pressures which can cause mechanical damage to the system are not required. Thus, the invention achieves major economic advantages and considerably improved patient convenience.

According to further embodiments of the method of the invention, the end portion of the catheter is extracted through the patient's abdominal wall, preferably by a laparoscopic procedure. The free end of the catheter should therefore be allowed at implantation to be relatively long in the peritoneum, the length being determined to a certain extent by the thickness of the patient's abdominal wall, e.g., 10 cm.

In order to facilitate the location of the catheter tip, the catheter, according to embodiments of the method of the invention, can be made opaque or opalescent to x-rays or can be provided with metal rings at suitable intervals along its length. If the catheter tip is made of metal, it can be observed easily by fluoroscopy, and incisions can be made close to the catheter tip without any risk of damage to the catheter.

According to another embodiment of the method of the invention, the cleaning fluid includes aggressive liquids, such as NaOH and enzymes, for chemical dissolution of plugs of medication, body protein etc. constituting catheter occlusions. As a result of this chemical dissolution of the stoppages, no increased pressure is required for mechanical cleaning and by virtue of the chemical dissolution the interior surface of the catheter becomes completely clean and free from sources which could give rise to new deposits. This embodiment is especially suitable for partial occlusions, i.e., when there is a flow obstruction but not complete catheter blockage. A flow of active fluid can then be achieved through and past the occlusion or blockage, which is eroded and dissolved.

When a catheter is completely blocked, getting the active liquid to the blockage may be difficult because of the long and narrow catheter in which it is difficult to achieve liquid exchange. According to an embodiment of the method of the invention, a negative pressure can then be applied to the syringe with which cleaning fluid is supplied into the flushing port, whereupon normal pressure of about 1 bar is again applied to the syringe, which procedure is repeated a number of times. When such a negative pressure, which is less than the vapor pressure of water at 37° C., is applied, vapor bubbles in the catheter will accordingly expand, and the liquid in the catheter upstream of the blockage is sucked into the syringe and mixed with the active fluid. When the pressure returns to the normal value, active liquid is sucked into the catheter completely up to the blockage, and the blockage starts dissolving. Further, by alternatingly applying a positive pressure to the syringe, according to yet another embodiment of the method of the invention, a combined chemical and mechanical action on the catheter occlusion is obtained.

The cleaning can be made even more effective, according to another embodiment of the method of the invention, by arranging a source of ultrasound in the syringe with which the cleaning fluid is supplied. In this way agitation of the fluid in the catheter is produced, thereby achieving more rapid exchange with the active fluid in the syringe.

According to a further embodiment of the method of the invention, the catheter, the external parts of the pump and the flushing port are back-filled with a neutral liquid after the catheter has been flushed with cleaning fluid in order to remove the latter fluid. Thereafter, these parts of the infusion system are back-filled with medication and the pump is made to pump of the maximum flow rate for a certain period of time before the catheter orifice is reinserted into the patient's peritoneum, or alternatively before it is opened in the peritoneum. This ensures that the patient receives the correct medication concentration immediately from the first pump stroke after the catheter has been cleaned.

According to other versions of the method of the invention, a cleaning wire can be inserted into the catheter through its orifice or through the flushing port to clean the catheter mechanically. The tip or the entire cleaning wire can advantageously be provided with a soft, low-friction coating to prevent scratching of the catheter surface. A neutral or active cleaning fluid can be supplied pressurized to a positive pressure through the flushing port into the catheter in order to form a supporting, lubricating film for the cleaning wire. This fluid, at positive pressure, also prevents any occlusion particles from being conveyed into the flushing port, from which they could subsequently reenter the catheter and cause new occlusions.

According to another version of the method of the invention, the cleaning wire is gradually inserted into the catheter by an oscillating, thrusting movement and/or with continuous or oscillating rotation around its axis, thereby preventing wire kinking.

DESCRIPTION OF THE PREFERRED EMBODIMENTS

Figure 1:
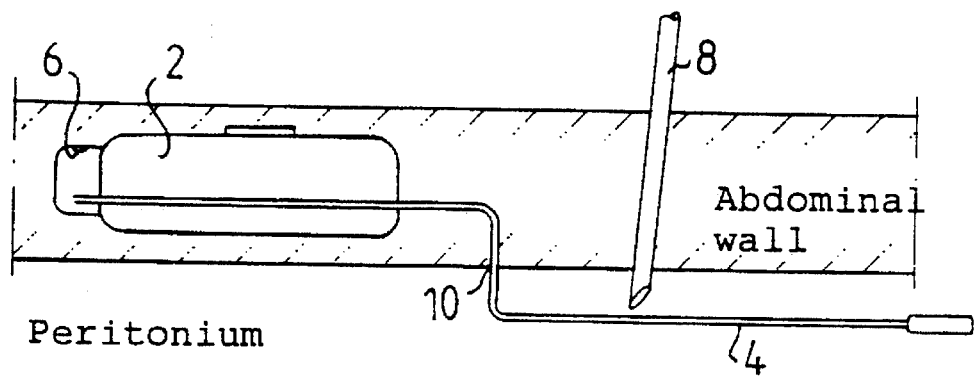
FIG. 1 shows a known medication infusion system implanted in the abdominal wall and with an endoscope inserted through the abdominal wall to the catheter as a first step in one embodiment of the inventive method.

FIG. 1 shows a known medication infusion system 2 implanted in the abdominal wall of a subject. The infusion system 2 comprises a medication container and a pump for pumping medication from the medication container into the patient via a catheter 4 connected to the output of the pump. The infusion system 2 further comprises control electronics and a battery as a source of power. These parts of the infusion system 2 are not shown specifically because they do not constitute any direct part of the present invention.

A flushing port 6 is arranged downstream of the pump and upstream of the catheter 4, through which a cleaning fluid can be flushed into the catheter 4. The cleaning fluid is normally a liquid but can also be a gas.

Under local anesthesia, a small diameter endoscope 8 can be inserted through the abdominal wall close to the point 10 at which the catheter enters the peritoneum. The catheter 4 can then be easily located through the endoscope 8, and the end of the catheter can be "fished out" with an appropriate instrument inserted alongside the endoscope 8 through the same incision and monitored with the endoscope 8. In order to increase the working space for the endoscope 8 in the peritoneum, the abdominal cavity can be inflated with carbon dioxide according to a known technique.

Figure 3:
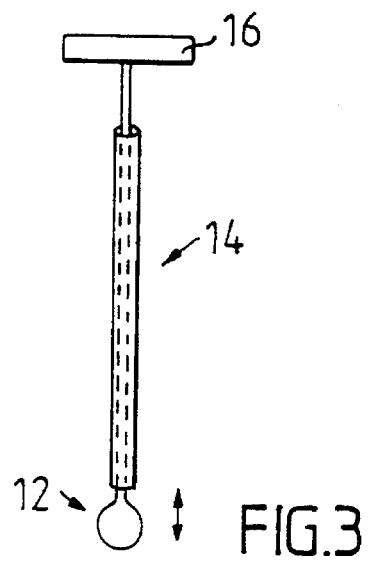
FIG. 3 shows an example of an instrument for extracting the end of the catheter in the method of the invention.

An appropriate instrument for picking up the end of the catheter 4 and pulling it out through the abdominal wall is a small biopsy tongs, a suitable loop of metal wire or the like. FIG. 3 shows such an instrument, in the form of a loop 12 of thin metal wire, arranged inside a tube 14 and attached to a handle 16. Another suitable instrument would be a surgical tool shaped as a small crochet-needle for pulling the end of the catheter 4 through the abdominal wall.

The procedure can advantageously be followed on a monitor connected to a video camera with attendant optics according to known endoscopic techniques.

In order to further facilitate the locating of the catheter tip, the catheter 4 can be made opaque or opalescent to X-rays or be provided with metal rings at appropriate intervals along its length. If the catheter tip in addition is made of metal, it can be easily monitored by radioscopy, and incisions can be made close to the catheter tip without any risk of damage to the catheter 4.

If the catheter 4 is not completely occluded but is only partially blocked, x-ray contrast medium, e.g., iodine solution or radioactive technetium, which is scintigraphically visible in the catheter 4, can be supplied through the flushing port 6 to make the catheter 4 visible.

Figure 2:
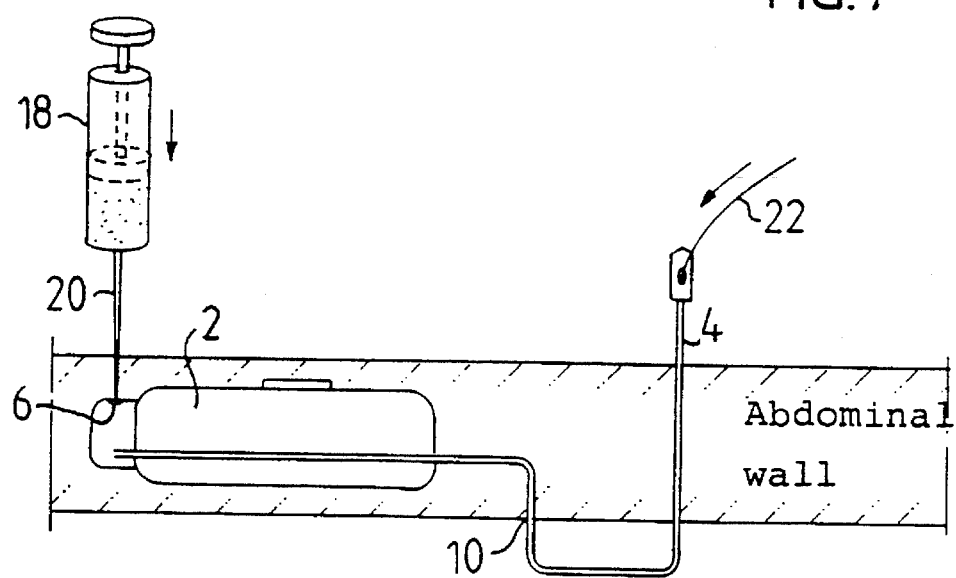
FIG. 2 shows the infusion system of FIG. 1 with the catheter end pulled out through the abdominal wall and a flushing syringe connected to the flushing port of the infusion system in accordance with the method of the invention.

With the catheter tip outside the abdominal cavity, as shown in FIG. 2, aggressive liquids can be used, e.g., NaOH with a pH less than 11, or enzymes, etc. for chemical dissolution of plugs of insulin, body proteins, etc. forming catheter occlusions. The procedure must of course be conducted under sterile conditions.

The cleaning fluid, appropriately a liquid, is injected into the flushing port 6 using a syringe 18 and a transcutaneous cannula 20 and is collected at the catheter orifice outside the patient, see FIG. 2. High pressures which are required for mechanical expulsion of catheter occlusions and which could damage the system are unnecessary. Since fluids capable of dissolving the plug and deposits on the interior of the catheter 4 are used, the catheter 4 becomes completely clean and free from "seeds" which could give rise to new blockages. The procedure is especially effective in the case of partial occlusions, i.e. when the flow is obstructed but there is no complete catheter blockage. There will then be a flow of active liquid through and past the occlusion, thereby eroding and dissolving the occlusion.

When the catheter 4 is completely blocked, a negative pressure, less than the vapor pressure of water at 37° C., i.e., less than about 63 mbars, can be applied to the flushing syringe 18. Vapor bubbles in the catheter 4 then expand, and liquid in the catheter 4 upstream of the blockage is sucked into the syringe 18 where it mixes with the active fluid.

When the pressure returns to the normal value, about 1 bar, active liquid is sucked into the catheter 4 completely to the blockage and can start to dissolve the blockage. Cyclical repetition of this procedure a number of times leads to an exchange of liquid at the blockage, and conditions for dissolving the blockage are created. Pressure cycling can be manual or automatic with a pump device which varies the pressure in cycles at an appropriate frequency. In this manner, a combination of chemical and mechanical action removes the blockage without pressure stresses exceeding about 1 bar. The procedure for cyclical pressure variation could, however, possibly utilize a slight positive pressure, on the order of a few bars, which the system could tolerate without risks.

The cleaning procedure can be further refined by providing a source of ultrasound (not shown) in the flushing syringe 18. This source of ultrasound will emit ultrasonic pressure waves in the liquid in the catheter 4, causing agitation of the liquid in the catheter, thereby achieving a faster exchange with active liquid in the syringe 18. The ultrasonic energy accordingly accelerates the requisite exchange of liquids at the occlusion interface.

The above measures can be combined to advantage as necessary.

After the occlusion or blockage has been removed, the flushing port, external parts of the pump and the catheter are suitably back-filled with a neutral liquid to remove the chemically active liquid, after which these parts are back-filled with insulin to ensure that the patient receives the correct concentration of insulin immediately from the first pump stroke after the catheter 4 is returned to its position in the peritoneum. Instead of this back-filling, insulin can be filled through the flushing port after catheter cleaning has been completed.

A cleaning wire 22 can be inserted into the catheter 4 for mechanical removal of the catheter occlusion. The wire 22 consists of a thin, typically 0.2 mm in diameter, relatively stiff wire, made of metal, a polymer material or some other suitable material, with a rounded tip to prevent damage to the inner lumen of the catheter 4. The tip of, and possibly the entire, cleaning wire 22 can advantageously be given a soft, low-friction coating, such as Teflon®, to prevent scratching of the catheter surface. A constant, appropriately high positive pressure with neutral or active liquid can be applied by means of the syringe 18 in the flushing port 6, see FIG. 2. The liquid then forms a supporting, lubricating layer for the cleaning wire 22 and thus reduces the risk for scratching of the inner surface of the catheter 4. The positive pressure also prevents any particles loosened from the occlusion from being carried back into the flushing port 6, from which they could subsequently reenter the catheter 4 and cause new blockages. The cleaning should therefore be performed in several stages.

Thus, the cleaning wire 22 is first moved a short distance into the catheter 4, and is then withdrawn at the same time as loose particles are flushed out by means of the syringe 18 in the flushing port 6. The cleaning wire 22 is then moved further into the catheter, again withdrawn etc. The cleaning wire 22 should be somewhat shorter than the length of the catheter 4, or alternatively can be equipped with a stop or marking, so the tip does not reach to the flushing port 6. This is to prevent particles from the catheter blockage from being pushed into the flushing port 6.

After the mechanical cleaning, the catheter can be flushed with active cleaning liquid to remove surface residues and films adhering to the interior of the catheter 4 which could serve as sources for new catheter occlusions, as discussed above.

When the catheter 4 has been cleaned and all deposits removed, the interior of the catheter 4 can be advantageously given a coating of surfactant using the syringe 18 in the flushing port 6, to prevent, e.g., the deposition of insulin, adsorption of proteins peculiar to the body, the adhesion and growth of body cells or bacteria, etc. After this surface treatment, the catheter can be rinsed with a neutral liquid and back-filled with insulin, as described above.

The catheter tip, which can be advantageously made of pure titanium but also of other materials, should suitably be especially devised for facilitating insertion of the cleaning wire 22.

Figure 4:
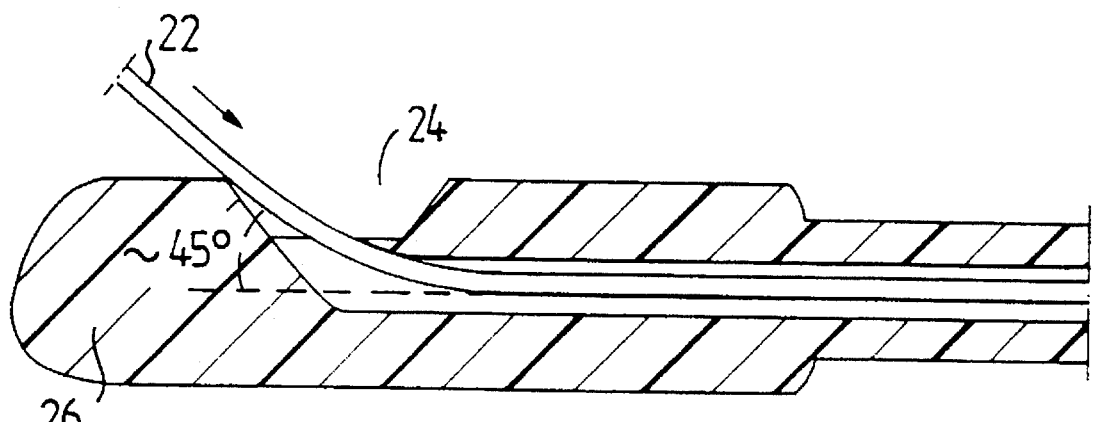
FIG. 4 shows the tip of a known catheter with a cleaning wire inserted as a step in another embodiment of the invention.

It has been found to be advantageous for catheters of the present kind to have the orifice 24 on the side of the catheter tip 26, a so-called lateral port, instead of an axial orifice. FIG. 4 shows such a catheter tip 26 which, however, is not very suitable for the insertion of a cleaning wire 22 because of its geometric shape, because the turning radius is too small.

Figure 5:
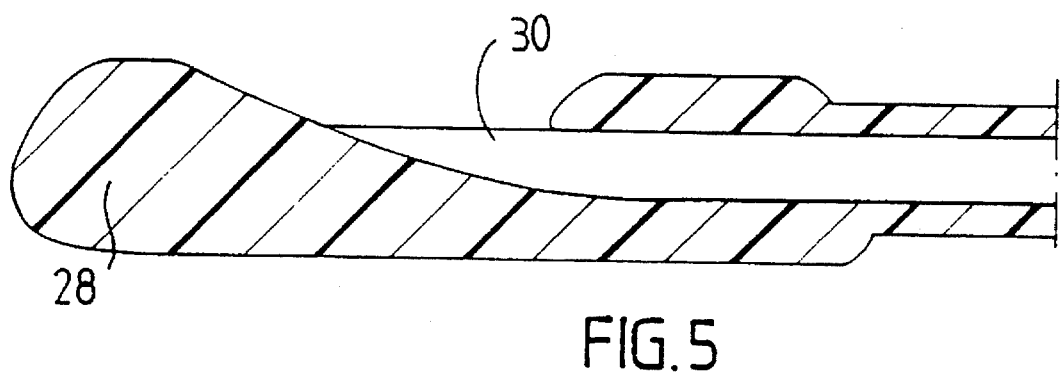
FIGS. 5 and 6 respectively show two versions of the catheter tip modified to facilitate the insertion of a cleaning wire.

FIG. 5 shows a modified catheter tip 28 which still has a lateral opening 30 but with its geometry modified to minimize friction when the cleaning wire 22 is inserted.

Figure 6:
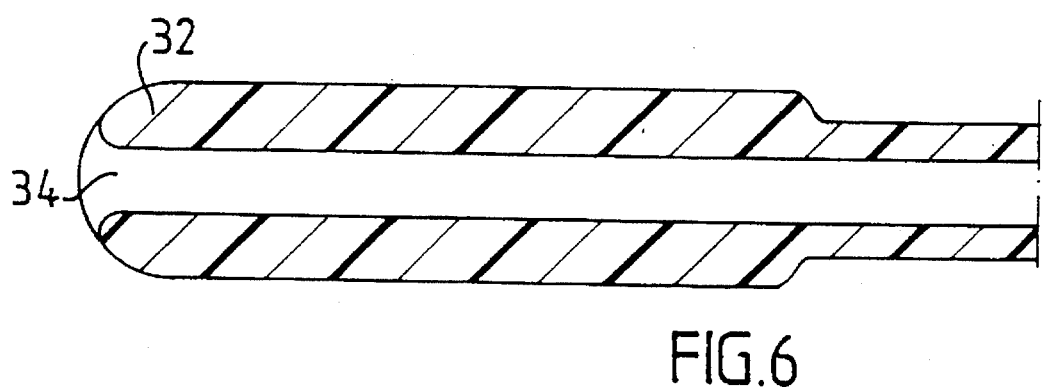

FIG. 6 shows another modified catheter tip 32 with an axial orifice 34 which is highly suitable for the insertion of a cleaning wire 22, but which does not have the advantages of the lateral port.

When a catheter blockage has been remedied, as described above, and the system has been refilled with insulin, the catheter tip is returned to the abdominal cavity, with the aid of a guide, through the tiny endoscopic incision, whereupon only a small compress dressing without sutures is sufficient. The patient can leave the hospital immediately, and no new appointment is necessary.

Figure 7:
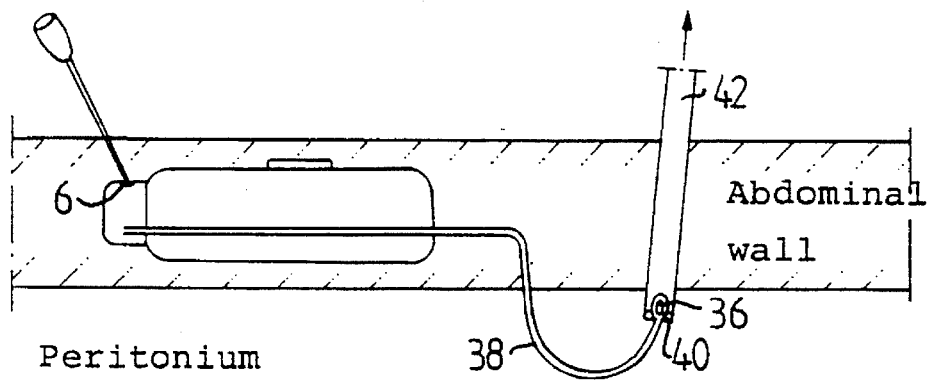
FIG. 7 shows an alternative version of the method of the invention, wherein a special instrument is introduced through the abdominal wall and establishes a leak-proof connection to the catheter orifice.

FIG. 7 shows an alternative solution in which taking the catheter tip out of the abdominal cavity is unnecessary.

In the embodiment illustrated in FIG. 7, a laparoscope/endoscope is inserted near the tip of the catheter in the same way as described above. This specially designed instrument is devised as a conduit member 42 which can be slipped over the tip of the catheter and sealed around it upstream of the catheter orifice 36, or sealed around the catheter 38 itself upstream of the catheter tip. The sealing can be accomplished with an expanding O-ring 40, an inflatable rubber cuff or the like. When active cleaning liquids are injected into the flushing port 6, the liquids and products loosened from the catheter occlusion are sucked out through the instrument or the conduit member 42.

Figure 8:
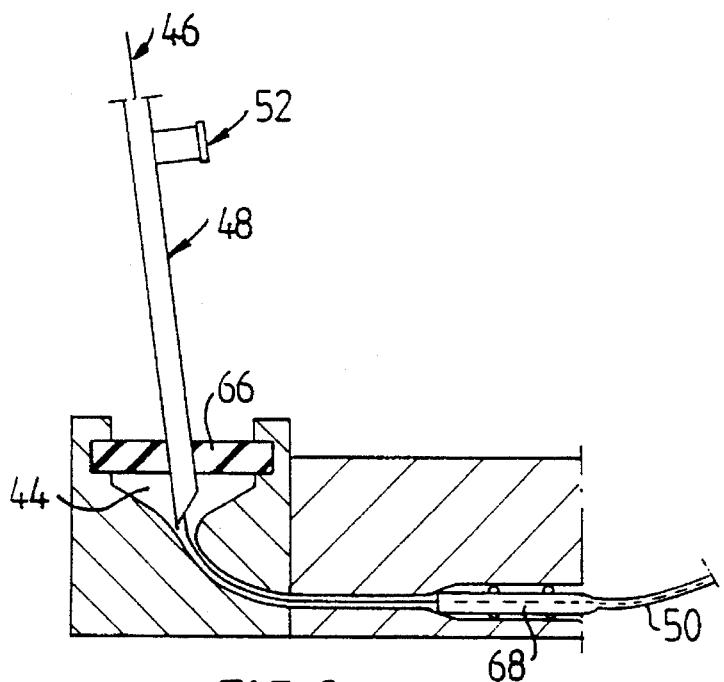
FIG. 8 shows a special construction of the flushing port to enable insertion of a cleaning wire at the same time as the catheter is flushed with cleaning liquid in the inventive method.

As a result of the special design of the flushing port 44, a cleaning wire 46 can also be introduced through a cannula 48 and into the catheter 50 for mechanical removal of a catheter occlusion, see FIG. 8. With an extra coupling or forked connector 52 on the cannula 48, cleaning with a cleaning wire 46 and flushing with a neutral or active liquid or gas can be performed simultaneously. It is important to avoid sharp bends in the cleaning wire channel to reduce friction on the cleaning wire 46 and to prevent kinking. The rubber septum covering the flushing port is shown at 66, and the catheter connection is shown at 68.

One effective way of manipulating the cleaning wire 46 is as follows:

The cleaning wire is gradually and slowly advanced into the catheter or catheter orifice with a thrusting or oscillating movement with an amplitude of, typically, 0.1–1 mm at the same time as the wire 60 is rotated around its axis, either continuously or in the form of an oscillating rotation. This is achieved with a special drive mechanism 54 and chuck 56 which automatically perform the described wire feed in direct conjunction with the cannula 58, see FIG. 9. This equipment is possibly mechanically connected to the cannula 58.

Figure 9:
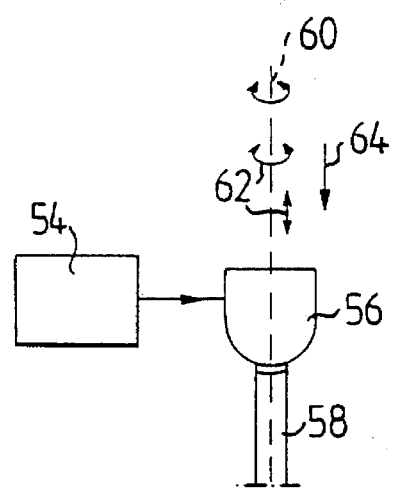
FIG. 9 shows a device for rotating and/or oscillating the cleaning wire during its insertion into the cannula and catheter in the inventive method.

In FIG. 9, the arrows 62 illustrate the advancement, the return and rotating movements of the cleaning wire 60, and the arrow 64 shows the general advancing direction of the cleaning wire 64.

In this way, the cleaning wire 60 is advanced into the catheter and removes catheter occlusions without kinking. By continuous flushing during this cleaning procedure a supporting, lubricating layer of liquid is obtained between the cleaning wire 60 and the catheter interior, thereby avoiding scratches and other damages to the catheter surface. This is important, since scratches could attract insulin deposits and initiate new occlusions, as noted above.

Flushing fluid, particles and other products of the cleaning are evacuated through the conduit member 42 using a negative pressure. The cleaning wire 60 is long enough to traverse the entire catheter and extend beyond the catheter tip by a certain margin. The cleaning wire can advantageously have a marking showing when the wire has been advanced through the entire catheter.

Thus, the method according to the invention achieves a number of important advantages. Any flushing fluid can be used without risk to the patient. Harmful high pressures do not have to be used. The patient is isolated from the cleaning pathway throughout the entire procedure, and no products of cleaning, crystals, modified insulin, particles, etc. capable of inducing the formation of antibodies, immune responses, macrophage accumulation, irritation etc. can enter the patient is abdominal cavity. There is no risk of occlusion of the lateral port of the catheter tip by products of the cleaning. The patient avoids the extra bolus dose of about 10 U being dispensed when flushing according to known methods. After cleaning is completed, the system is flushed with a neutral liquid, possibly the catheter is treated with a surfactant and finally it is back-filled with insulin, as described above, so the patient receives the correct insulin concentration immediately from the first pump stroke when infusion is resumed. Thus the patient avoids the period of latency which follows known flushing procedures before the insulin concentration has returned to the normal level. Moreover, the surgical operation is minimal surgery and the patient can leave the hospital immediately after the operation, and does not need a new appointment to remove stitches. In addition, the risk of infection, which is always present when the implant pocket is opened for a catheter exchange, which has heretofore often been necessary when catheter occlusions occur, is avoided. The presence of infection often makes necessary explantation of the implant and establishment of a new pocket at another site.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for cleaning the catheter of an implanted medication infusion system having a medication container and a pump for pumping medication from the medication container into a patient via said catheter, and a flushing port disposed downstream of said pump and upstream of said catheter through which a cleaning fluid can be flushed through said flushing port into said catheter, said catheter having an orifice and terminating in a catheter tip, said method comprising the steps of:

placing said orifice of said catheter in fluid communication with an exterior of said patient; and flushing cleaning fluid through said flushing port and through said catheter while said orifice is in fluid communication with the exterior of the patient and discharging said cleaning fluid from said catheter tip to the exterior of said patient.

2. A method as claimed in claim 1 wherein the step of placing said orifice of said catheter in fluid communication with the exterior of said patient comprises extracting a portion of said catheter, including said catheter tip, through the abdominal wall of said patient to the exterior of said patient.

3. A method as claimed in claim 2 wherein the step of extracting said portion of said catheter through the abdominal wall of said patient comprises extracting said portion of said catheter through the abdominal wall of said patient by a laparoscopic procedure.

4. A method as claimed in claim 1 wherein the step of placing said orifice of said catheter in fluid communication with the exterior of said patient comprises inserting a conduit member through the abdominal wall of said patient and sealing an end of said conduit member around said catheter in situ in said patient.

5. A method as claimed in claim 4 comprising the additional step of applying a negative pressure to an end of said conduit member disposed at an exterior of said patient while flushing said cleaning fluid through said catheter.

6. A method as claimed in claim 4 comprising the additional step of injecting a physiologically compatible sodium chloride solution into said abdominal cavity in an area surrounding said catheter tip before flushing said cleaning fluid through said catheter.

7. A method as claimed in claim 1 comprising the additional step of making at least a part of said catheter opaque to x-rays for facilitating location of said catheter tip.

8. A method as claimed in claim 1 comprising the additional step of making at least a part of said catheter opalescent to x-rays for facilitating location of said catheter tip.

9. A method as claimed in claim 1 comprising the additional step of disposing metal rings at selected intervals along a length of said catheter for facilitating x-ray location of said catheter tip.

10. A method as claimed in claim 1 comprising the additional step of making said catheter tip of metal for facilitating x-ray location of said catheter tip.

11. A method as claimed in claim 1 comprising the additional step of selecting said cleaning fluid from the group of aggressive liquids consisting of NaOH and enzymes.

12. A method as claimed in claim 1 comprising the additional step of alternatingly subjecting said cleaning fluid while being flushed through said flushing port and said catheter to a first pressure, not less than atmospheric pressure, and a second pressure which is a negative pressure.

13. A method as claimed in claim I comprising the additional step of alternatingly subjecting said cleaning fluid while being flushed through said flushing port and said catheter to a first pressure, greater than atmospheric pressure, and a second pressure which is a negative pressure.

14. A method as claimed in claim 1 comprising the additional step of subjecting said cleaning fluid to ultrasound vibrations while flushing said cleaning fluid through said flushing port and said catheter.

15. A method as claimed in claim 1 comprising the additional steps of:

back-filling said catheter, said pump and said flushing port with a neutral liquid after flushing said cleaning fluid through said flushing port and said catheter for removing said cleaning fluid;

replacing said neutral liquid by back-filling said catheter, said pump and said flushing port with medication; and operating said pump to pump at a maximum flow rate for a selected time before reinserting said portion of said catheter into said patient.

16. A method as claimed in claim 1 comprising the additional step of inserting a cleaning wire into said catheter through said orifice from the exterior of said patient.

17. A method as claimed in claim 16 wherein the step of inserting said cleaning wire into said catheter comprises inserting said cleaning wire into said catheter with a thrusting, oscillating movement.

18. A method as claimed in claim 17 comprising the additional step of rotating said cleaning wire while inserting said cleaning wire into said catheter.

19. A method as claimed in claim 16 comprising the additional step of applying a soft, low-friction coating said cleaning wire prior to insertion into said catheter.

20. A method as claimed in claim 16 comprising the additional step of flushing said cleaning fluid through said flushing port and said catheter pressurized at a positive pressure.

21. A method as claimed in claim 1 comprising the additional steps of:

after flushing said catheter with said cleaning fluid, inserting a cleaning wire into said orifice of said catheter from the exterior of said patient up to a first distance for loosening particles in said catheter flushed by said cleaning fluid;

again flushing said catheter with said cleaning fluid;

inserting said cleaning wire a further defined distance into said catheter for loosening particles flushed by said cleaning fluid; and repeatedly flushing said catheter with said cleaning fluid and advancing said cleaning wire into said catheter after each flushing until said cleaning wire reaches a predetermined distance from said flushing port.

22. A method as claimed in claim 21 comprising the additional step of providing said cleaning wire with means for preventing said cleaning wire from being introduced into said catheter beyond said minimum distance from said flushing port.

23. A method as claimed in claim 1 comprising the additional step of injecting a surfactant through said flushing port after flushing said catheter with cleaning fluid to coat the interior of said catheter with said surfactant.

24. A method as claimed in claim 1 comprising the additional step of inserting a cleaning wire through said flushing port into said catheter.

* * * * *